United States Patent [19]

Brauer et al.

[11] Patent Number: 4,968,632
[45] Date of Patent: Nov. 6, 1990

[54] METHOD AND APPARATUS FOR RAPID ANALYSIS OF A SAMPLE MEDIUM

[75] Inventors: Stefan Brauer, Soedra Sandby; Jan Johansson, Stehag; Jan-Ove Nilsson, Täby; Sven G. Olsson, Villa Fortuna, all of Sweden

[73] Assignee: Siemens Aktiengesellschaft, Berlin and Munich, Fed. Rep. of Germany

[21] Appl. No.: 409,964

[22] Filed: Sep. 18, 1989

Related U.S. Application Data

[63] Continuation of Ser. No. 777,608, Sep. 19, 1985, abandoned.

[30] Foreign Application Priority Data

Sep. 19, 1984 [DE] Fed. Rep. of Germany ....... 3434423

[51] Int. Cl.⁵ ............................................. G01N 33/16
[52] U.S. Cl. .................................... 436/136; 436/172; 422/52; 422/91; 250/459.1
[58] Field of Search .................. 436/136, 172; 422/52, 422/68, 91; 250/458.1, 459.1, 432

[56] References Cited

U.S. PATENT DOCUMENTS

| | | | |
|---|---|---|---|
| 3,285,703 | 11/1966 | Narita | 422/52 |
| 3,612,866 | 11/1971 | Stevens | 436/136 |
| 3,725,658 | 4/1973 | Stanley et al. | 436/172 |
| 3,910,701 | 10/1975 | Henderson et al. | 356/39 |
| 4,003,707 | 1/1977 | Lubbers et al. | 356/39 |
| 4,150,951 | 4/1979 | Capelle et al. | 436/172 |
| 4,167,331 | 9/1979 | Nielsen | 356/39 |
| 4,495,293 | 1/1985 | Shaffar | 436/172 |
| 4,580,059 | 4/1986 | Wolfbeis et al. | 250/458.1 |

FOREIGN PATENT DOCUMENTS 0091390 10/1983 European Pat. Off. .
3148830 6/1981 Fed. Rep. of Germany .

OTHER PUBLICATIONS

Fluoroptic Thermometry: Temperature Sensing Using Optical Fibers, Alves et al, Advances in Instrumentation, vol. 38, Oct. 198'pp. 925-932.

Primary Examiner—David Simmons
Assistant Examiner—Lori Johnson
Attorney, Agent, or Firm—Hill, Van Santen, Steadman & Simpson

[57] ABSTRACT

A method and apparatus for rapid analysis of a sample medium, particularly a flowing sample medium employ light of a defined wavelength which is guided onto a luminescent layer in contact with the sample medium, the luminescent properties of the layer varying in dependence upon characteristics of the sample medium which are to be analyzed. The luminescent light is monitored by detectors, the detector signals being a measure for the characteristic of interest. For undertaking identification of a particular characteristic with very short follow-up time, even in the presence of a number of other characteristics which influence the luminescent properties, the luminescent intensity is identified for a number of different wavelength regions corresponding in number to the number of characteristics, each characteristic differently influencing the luminescent properties in at least one wavelength region. The signals thus obtained are supplied to a processing device for identifying the value of the characteristic of interest.

30 Claims, 3 Drawing Sheets

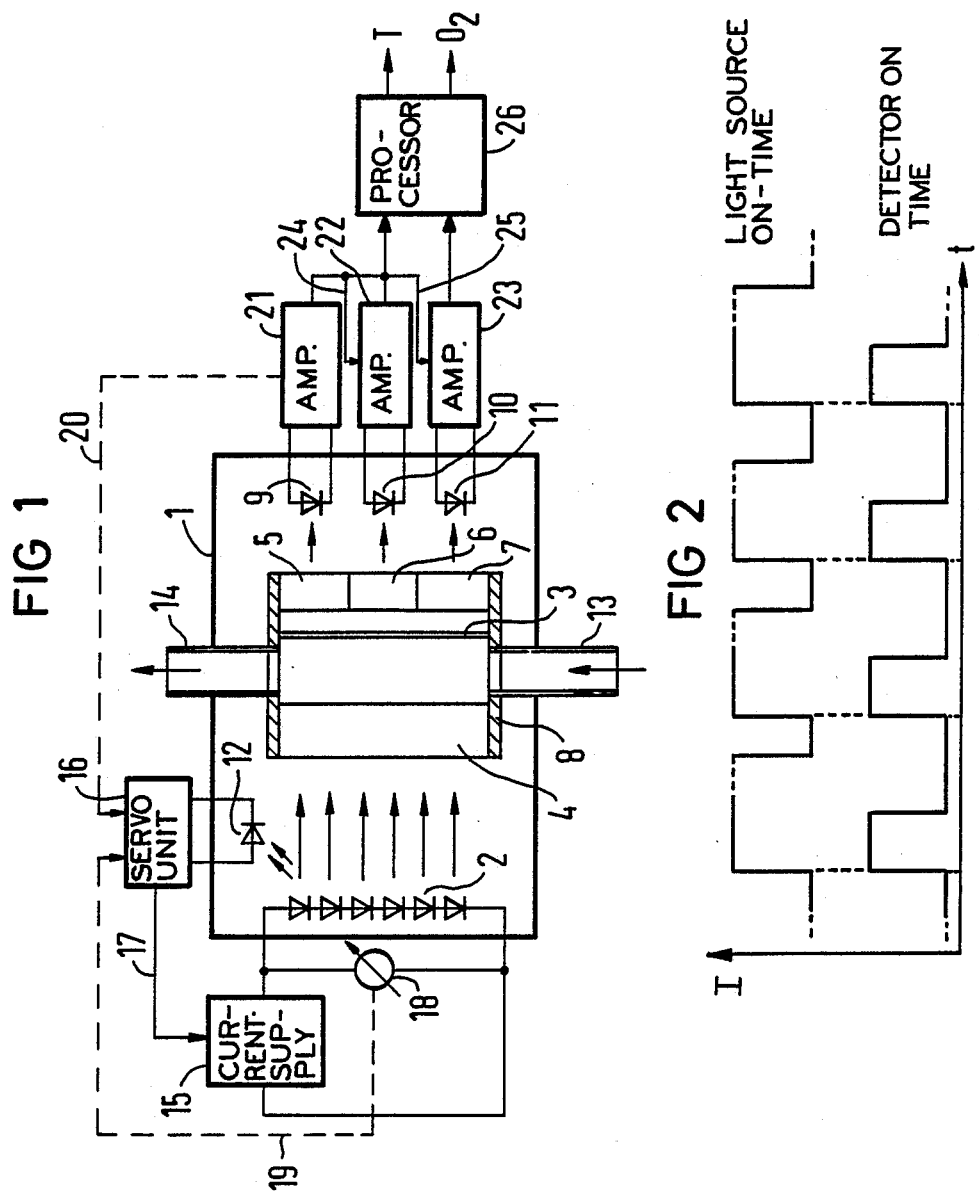

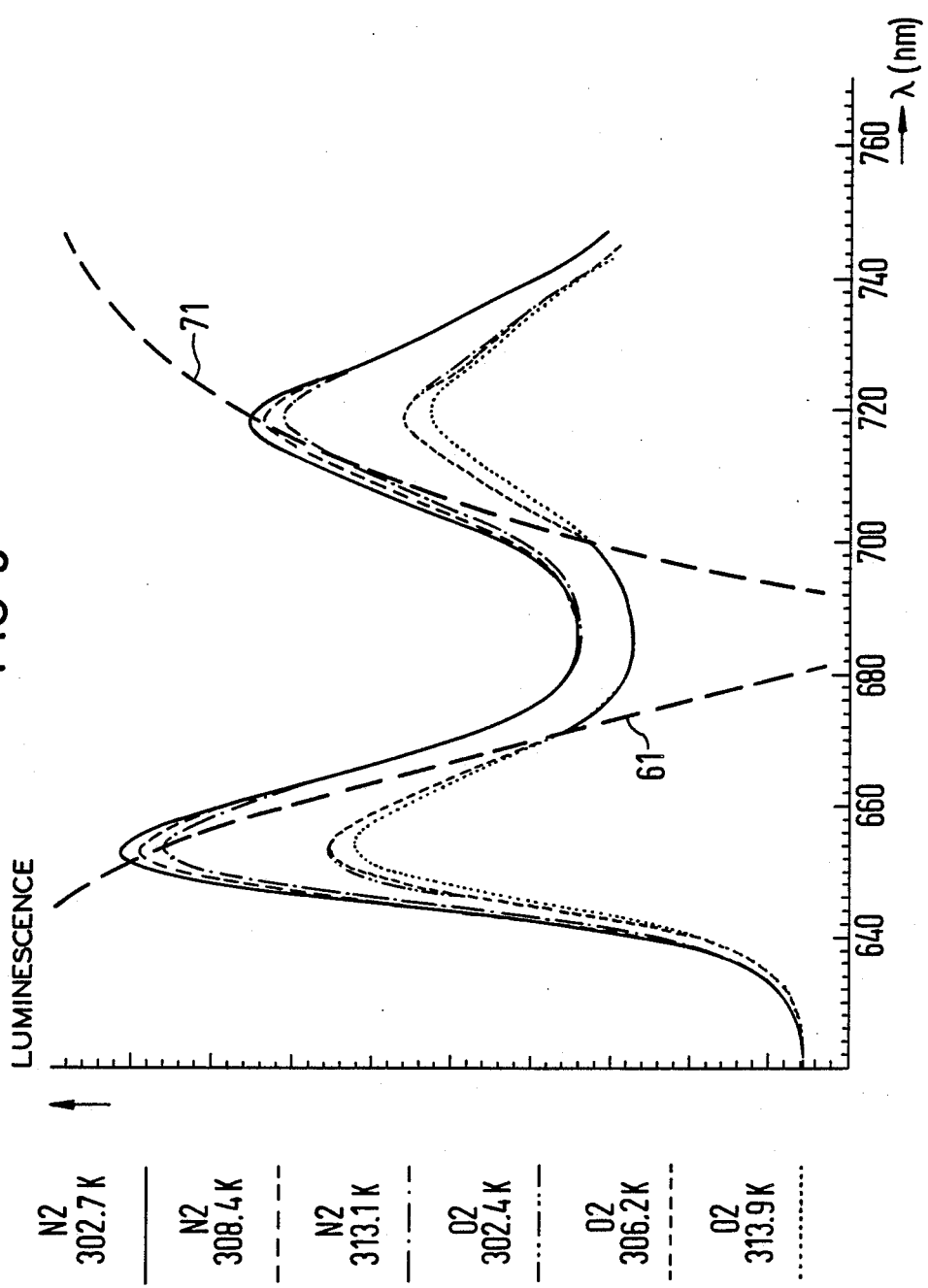

METHOD AND APPARATUS FOR RAPID ANALYSIS OF A SAMPLE MEDIUM

This is a continuation, division, of application Ser. No. 777,608, filed Sep. 19, 1985 now abandoned.

BACKGROUND OF THE INVENTION

1. Field Of The Invention:

The present invention relates to methods and devices for rapidly analyzing characteristics of a sample medium, and in particular to such methods and devices for identifying characteristics of a flowing sample medium by the interaction of the sample medium with a luminescent layer.

2. Description Of The Prior Art

A method is described in German No. OS 31 48 830 for identifying at least one characteristic of a flowing sample medium by directing light of a known wavelength onto at least one luminescent layer which is directly or indirectly in contact with the sample medium. The luminescent properties of the layer change in dependence upon the characteristics of the medium, and the resulting luminescent light is supplied to detectors whose signals are a measure for the characteristic to be identified In many instances, the measurement of the oxygen concentration in fluids (gases and liquids) must be undertaken with extremely short follow-up time of a few milliseconds, and with no "dead time" and the measurement must be undertaken such that no oxygen is consumed in the measurement. For example, the oxygen concentration in the expiration air for respiratory treatment of patients should ideally be monitored in this manner.

The principle of luminescence quenching of layers excited to luminesce with light of a defined wavelength has been used for undertaking measurements with short follow-up times. Investigations have shown, however, that the luminescent properties of such layers are influenced not only by oxygen, but also by other characteristics or components of the fluid. For example, temperature changes the intensity of the luminescent light in the same manner as oxygen, i.e., the amplitude of the emitted light decreases with increasing temperature. Moreover, increasing temperature also causes a shift toward longer wavelengths. Humidity and water also influence luminescent properties. In the specific case of respirator treatment, the influence of anesthesia gases, such as nitrous oxide or halothane, are also of consequence.

In general terms, a number of different substances exist which influence specific luminescent layers. The response of the luminescent layers to such substances generally depends upon the selected combination of carrier material and luminescent dyestuff. Flowing sample media such as gases and other fluids are employed as the sample media. This does not, however, exclude other sample media. The principle of luminescent quenching can be utilized for undertaking such measurement as long as the luminescent layer is influenced by the characteristic of the sample medium which is of interest.

The additional influences on the luminescent light by other characteristics were hitherto considered to be insurmountable difficulties for undertaking fast measurement of oxygen concentration in this manner. In order to eliminate the influence of humidity, the luminescent layers were shielded from the sample medium by a membrane as taught in U.S. Letters Patent 4,003,707. As a result, however, the follow-up time was greatly increased given the layers employed, so that this known measuring device is not suitable for rapid identification of the oxygen concentration in, for example, patient monitoring.

The influence of temperature on the luminescent layers has also been investigated, but only for the purpose of actually sensing the temperature as the characteristic of interest. The temperature effect is considered disturbing in the identification of oxygen in respiratory gases, and attempts were made to eliminate this influence by bringing the respiratory gas to a predetermined temperature before analysis thereof. Under certain conditions, a defined humidity was also set at the same time. These measures, however, also resulted in an undesirably high follow-up time.

Although luminescent layers having water repellant carrier material, whose luminescent properties are therefore not influenced by humidity, are known from the aforementioned German OS No. 31 48 830, the temperature effects nonetheless remain.

SUMMARY OF THE INVENTION

It is an object of the present invention to provide a method and apparatus for rapid analysis of a sample medium, such as measurement of the oxygen content of a fluid, using the principle of luminescent quenching which achieves a reliable identification of the characteristic of interest within an extremely short follow-up time, even in the presence of a number of different characteristics which also influence the luminescent properties of the luminescent layer employed.

It is a further object of the present invention to identify at least one further characteristic simultaneously with the first characteristic of interest.

The above object is inventively achieved in a method and apparatus wherein the sample medium is brought into contact with a luminescent layer having luminescent properties which vary as a function of the characteristic of interest, as well as varying as a function of other characteristics of the sample medium. Light of a defined wavelength is directed at the luminescent layer, and the intensity of the emitted luminescent light is detected in a plurality of different wavelength regions, the number of different wavelength regions being equal to the number of the influencing characteristics of the medium. One of the wavelength regions is selected wherein the characteristic of interest and the other characteristics differently influence the luminescent intensity. The signals received in the different wavelength regions are supplied to a processor from which the characteristic of interest is identified and a value assigned thereto.

The method and apparatus disclosed herein make use of the influence on the luminescent properties caused by different characteristics which were heretofore considered disruptive for this purpose. The method and apparatus make use of such influences for undertaking a rapid measurement and identification of one characteristic, for example oxygen concentration, and also provide the option of identifying one or more further characteristics at the same time. As used herein, "rapid" means within a few milliseconds. In contrast to conventional methods and devices, no attempt is made in the method and apparatus disclosed herein to suppress the influence of the further characteristics. The additional luminescence influence of the further characteristics is identified and used for analyzing the characteristic of interest.

For implementing the above method, the intensity of the luminescent light must be identified for at least as many different wavelength regions as there are characteristics which influence the luminescent properties. At the same time, the wavelength regions must be selected such that at least one characteristic differently influences the layer properties in the different wavelength regions. In order to maintain the measuring outlay, as well as the outlay for identifying the characteristic of interest from the measured results, within justifiable limits, luminescent layers are selected which react to different combinations of characteristics and whose luminescent properties are independent of some of the characteristics. Thus, for example, luminescent layers may be used having luminescent properties dependent on only two parameters, such as the oxygen content and the temperature of the sample medium. When such a layer is combined with another layer, which may be additionally influenced by humidity, two characteristics can be identified by the first layer and can then be presumed as known for the second layer. Outlay for identification of the third parameter is thus substantially diminished.

The aforementioned U.S. Letters Patent 4,003,707 teaches undertaking luminescent quenching at a number of different wavelengths. The wavelength of the excitation light and the wavelength of the detected luminescent light are simultaneously varied. The different measured signals are supplied to a signal processor which determines only one characteristic from the incoming signals, and does not take disturbances due to other characteristics into consideration. Optical errors of the system, stray light effects, and individual measurement errors are merely eliminated by the various measurements.

In order to increase the measurement precision in the method and apparatus disclosed herein, a further embodiment maintains constant the spectral distribution and/or the intensity of the light incident on the luminescent layer by means of a control circuit. This enables the use of simple light sources such as, for example, light emitting diodes, which are particularly useful in mass production.

In a further embodiment of the method and apparatus, the intensity of light from the luminescent layer is identified in the wavelength region of the excitation light, and is used as a reference signal for correcting the luminescent intensities in the selected wavelength regions. Even when the intensity of the light source is constant, it cannot be guaranteed that the same quantity of light will always be incident upon the layer. It is therefore important to optimally suppress all disturbing effects, especially given the relatively small differences in intensity which are produced by the characteristics to be identified.

In the method and apparatus disclosed herein, the light is preferably guided onto the luminescent layer in pulses. This avoids drifting in the detectors and/or in the signal processing units because the components are reset to zero during the pauses between pulses. This is particularly advantageous given the use of light emitting diodes, because those components tend to heat excessively and thereby generate a different emission spectrum. The light pulses may alternatively be generated by a constantly powered light source in combination with an optical or mechanical chopper.

For identifying two characteristics in the signal processor, a formulation is utilized assuming that the incoming signals $S_i$ are composed of a background component, a component linearly dependent on one of the characteristics, and a component reciprocally dependent on the other characteristic, this being represented in the equation:

$$S_i = \frac{i_i}{1 + k_i X_1} + b_i X_2 + a_i$$

In the above equation, $i_i$ is the luminescent intensity at a defined wavelength $\lambda_i$ and given a specific value of the characteristic $X_1$ (particularly given $X_1=0$), $a_i$ is the background intensity, and $k_i$ and $b_i$ are approximation coefficients. The coefficient $k_i$ is a measure of the luminescence quenching for the characteristic $X_1$ when no other characteristics influence the luminescence. The coefficient $b_i$ indicates the extent to which the characteristic $X_2$ influences the signal $S_i$. The index i runs from 1 to 2 when measurement is undertaken with two luminescent wavelengths.

For improving the measuring precision, however, more than two wavelengths may be used. The outlay for signal evaluation, however, correspondingly increases.

Tests have shown that two characteristics can be very precisely identified by using the above equation. A different equation must be used to identify more than two characteristics.

In addition to the method of calculating two characteristics from the two detector signals, it is also possible to iteratively identify the characteristics from the detector signals, as discussed in greater detail below using an example.

In order to provide an apparatus for implementing the above method which does justice to the high demands made on reliability, particularly in the area of patient respiration monitoring, at least one light emitting diode is used as the light source. A characteristic of the light emitting diode is identified and used for driving the diode such that the temperature of the active diode region receives a defined current value, i.e., is operated at a defined portion of an operating curve. The intensity and the spectral distribution of the emitted light thus are substantially invariant. At least one filter is disposed between the light emitting diode and the luminescent layer for selecting the proper excitation wavelength from the emission spectrum of the light emitting diode.

As discussed above, other light sources may be equivalently used when conditions permit. A laser is always an excellent light source because of its high intensity and monochromatism. Laser diodes may be used when available at the required excitation wavelengths which have adequate stability and service life.

If the intensity and, under certain conditions, the spectral distribution of the emitted light fluctuate, these variations must be identified and correction of the detector signals must be undertaken.

Further filters may be disposed between the luminescent layer and the detectors. The apparatus must also include means for bringing the sample medium directly or indirectly into contact with the luminescent layer.

For boosting the intensity of the excitation light, given the use of light emitting diodes as the light source, and under given conditions to compensate unit fluctuations of individual light emitting diodes, the diodes may be connected in series or parallel. The signal-to-noise ratio may also be improved in this manner.

The light emitting diodes may be continuously operated in which case the voltage drop across the light emitting diodes is used for control purposes, and the current flowing through the light emitting diodes is set by this value. For avoiding drifting in the components which are used, the light emitting diodes may be briefly shut off at selected time intervals and all components balanced during these pauses.

As stated above, the light emitting diodes may be operated by pulsing, such as by constant current pulses. In this case, control of the light emitting diodes is undertaken by the pulse duration. The detectors register the intensity of the luminescent light only during a portion of the pulse duration. The length of the excitation pulse thus does not influence the measured signals. Another option is to vary the current during the pulses.

In a further embodiment of the invention the intensity of two wavelength regions of the light emitting diodes is measured and their quotient is used as the control parameter.

In order to further eliminate other disturbing influences such as dirty filters or the like, the registration time may be regulated dependent upon a reference signal. Light supplied from the luminescent layer in the wavelength region of the excitation light can serve as such a reference signal. For this purpose, a further detector may be provided, as well as a filter between the further detector and the luminescent layer. The measured signal of this reference detector can be directly used for controlling the registration time. It is also possible to integrate the signal of the reference detector and to end the registration when a prescribed integration value is reached. Operation in such a manner is one way of achieving automatic standardization.

In a further embodiment the measured signals of the detectors measuring the luminescent light of different wavelengths can be relatively balanced by dividing every measured signal by the signal from the reference detector before the measured signal is supplied to the signal processor.

In an embodiment of the method using light emitting diodes operated in a pulsed manner, on characteristic of the light emitting diodes is identified during the pulse, particularly at the beginning of the pulse, and is used for shaping the pulse. The chronological position of the measuring duration in which the detectors measure the luminescent intensity is defined in dependence upon the value of this characteristics. When the voltage drop across the diodes at the beginning of the pulse is used as this parameter, a measure of the temperature of the light emitting diodes can be obtained. A specific spectral distribution can then be set dependent on this temperature. If the temperature is too low, the pulse can be lengthened or the current can be boosted during the pulse. Both options will result in an increase in the diode temperature. If the temperature is too high at the beginning, opposite measures are undertaken. In both instances, a diode temperature corresponding to the desired spectral distribution will be established at a specific point in time within the pulse. If the time span for the luminescent measurement is within the region in which the light emitting diodes have the desired temperature, determined in dependence on the parameter measured at the beginning of the pulse, the desired spectral distribution having the same conditions will always be obtained, or at least the desired spectral distribution will be obtained on average.

For reducing outlay for avoiding disturbing influences, the light emitting diodes, filters, the luminescent layer, and the detectors may all be disposed in a light-tight housing.

DESCRIPTION OF THE DRAWINGS

FIG. 1 is a schematic diagram showing an apparatus for rapidly identifying at least one characteristic of a sample medium constructed in accordance with the principles of the present invention in practicing the method disclosed herein.

FIG. 2 is a voltage/time diagram showing pulses for operating the light sources and the detectors in the apparatus of FIG. 1.

FIG. 3 is an example of an emission spectrum for a luminescent layer of the type obtained in the apparatus shown in FIG. 1.

DESCRIPTION OF THE PREFERRED EMBODIMENTS

Figure 4:
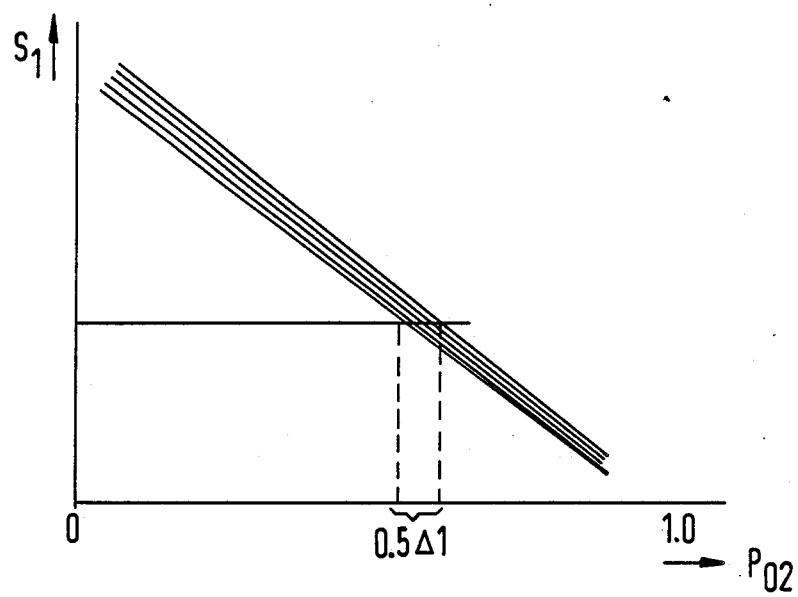
FIGS. 4 and 5 are graphs showing detector signal curves for two wavelengths dependent on the partial oxygen pressure and on the temperature.

An apparatus constructed in accordance with the principles of the present invention and using the method disclosed herein for identifying two characteristics of a fluid is shown in FIG. 1. The embodiment of FIG. 1 is for simultaneously identifying the oxygen concentration and the temperature of a gas. The apparatus includes a light-tight housing 1 having a plurality of light emitting diodes 2 connected in series, a transparent luminescent layer 3, and filters 4, 5, 6 and 7 disposed in a mount 8 in combination with the luminescent layer 3, and four photodiodes 9, 10, 11, and 12. The housing 1 and the mount 8 are provided with a gas intake 13 and a gas discharge 14. The direction of gas flow is indicated by the arrows, however, the gas may flow in either direction without affecting the operation of the device. The gas is conducted directly past the luminescent layer 3. This is schematically indicated in FIG. 1 and is not to scale. In order for the characteristic which is to be measured to be quickly varied at the luminescent layer 3, the gas intake 13 and the gas discharge 14 should be relatively large, and the volume between the filter 4 and the luminescent layer 3 should be small in comparison thereto The light emitting diodes 2 are operated in a pulsed manner by a current supply 15. The chronological path of the current is shown in the upper portion of FIG. 2 when pulsing is undertaken with constant current. That portion of the pulses which can be varied is indicated by dashed lines. Other pulse shapes may be selected as needed. Control of the power supply 15 is undertaken dependent upon a diode parameter. Various possibilities are indicated in FIG. 1. The intensity of the light emitted by the diodes 2 can be identified by a detector 12 and suppied to a servo device 16 which, as indicated by the arrow 17 drives the power supply 15. A further possibility is to measure the voltage drop across the light emitting diodes 2 with a voltmeter 18, and to supply the output of the voltmeter 18 to the servo device 16 for control of the power supply 15, as indicated by the dashed line 19.

Another possibility is to measure the intensity of the light passing through the luminescent layer 3 and through a filter matched to the wavelength region of the excitation light so as to be incident on a detector 9, which supplies a signal via dashed line 20 to the servo unit 16 for controlling the current supply 15.

As indicated by the dashed line connections, the diodes 2 can be operated in series or in parallel.

Regardless of the type of control or regulation, the spectral distribution and the intensity of the emitted light remain constant, or at least have a defined curve.

Filters 6 and 7 are provided active at different wavelength regions of the luminescent spectrum. Light passing through these filters is registered by respective detectors 10 and 11.

Amplifiers 21, 22 and 23 which may include integration means, differentiating means, and other elements are directly connected to the outputs of the detectors 9, 10 and 11. The amplifiers 21, 22 and 23 simultaneously define the pulse duration for registration of the signals received from the detectors, as indicated in the lower portion of FIG. 2 wherein the pulse width for registration of the luminescent light is shown smaller than the smallest pulse width of the excitation light.

If the signal from the detector 9 is defined by the amplifier 21, this signal can be forwarded by lines 24 and 25 to the amplifiers 22 or 23 in which the signal value of the detectors 10 and 11 are then formed standardized to the intensity of the excitation light.

The output signals of the two amplifiers 22 and 23 are supplied to a signal processor 26 which identifies the desired values, i.e., oxygen concentration and the temperature of the gas, from the incoming signals.

For further explaining the subject matter of the invention, the emission spectrum of a typical luminescent layer and its dependency on the characteristics of oxygen concentration and temperature are shown in FIG. 3. The conditions for the various curves are specified at the left of FIG. 3. The luminescent spectrum has two emission maxima, one at roughly 655 nm, and the other at 720 nm. The excitation light has a shorter wavelength. As can be seen in FIG. 3, a substantial luminescence quenching occurs as a result of the presence of oxygen. Increasing temperature causes an effect acting in the same direction which is, however, less pronounced. Additionally, a shift of the luminescent maxima toward higher wavelengths also occurs with increasing temperature, independently of the oxygen concentration. Because rapid temperature fluctuations over several degrees Celsius may occur in the expired air during respirator treatment of patients, rapid oxygen concentration measurement in the expiration phase was heretofore not possible.

This problem is overcome in the method and apparatus disclosed herein by measuring a luminescent light in two wavelength regions. For example, FIG. 3 shows the upper band edge 61 of the filter 6 and the lower band edge 71 of the filter 7 with dashed lines. If, for example, a temperature elevation occurs, the first luminescent maximum moves from the transparency region of the filter 6, and the second maximum moves into the transparency region of the filter 7. Rather different modifications of the signals of the detectors 10 and 11 result therefrom given a change in temperature. The detector signal $S_1$ derives according to the equation for two parameters, in this case the oxygen concentration, which can be expressed as the partial oxygen concentration $p_{O2}$, given a known pressure, and a temperature T $$S_1 = \frac{i_1}{1 + k_1 p_{O2}} + b_1 T + a_1$$

The detector signal $S_2$ is similarly derived. When the coefficients are identified by means of various calibrations, the values for the two parameters T and $p_{O2}$ can be identified by the signal processor 26 from these two equations. The coefficients in the equation for $S_2$ may assume different values than in the equation for $S_1$. Certain coefficients must be determined by calibrations whereas others may have fixed values.

Figure 5:
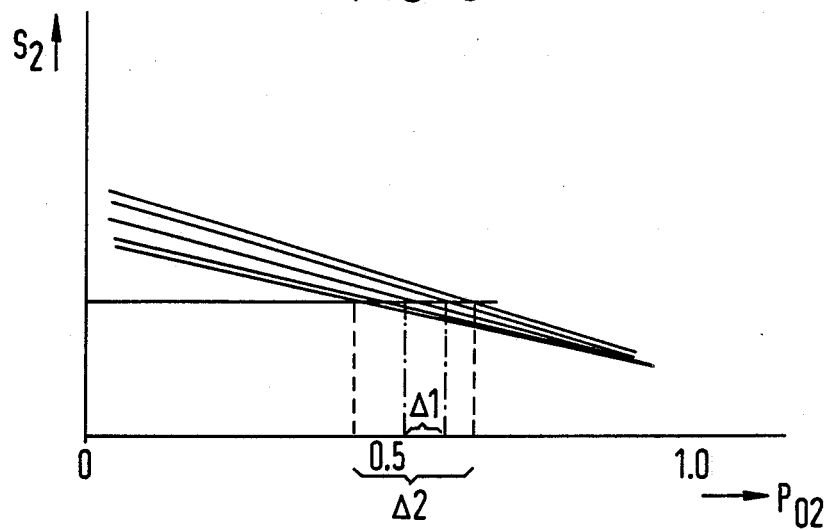

As mentioned above, the two parameters may also be iteratively identified. This method is explained in connection with FIGS. 4 and 5. The curve of the measured signals from the detectors 10 and 11 is entered in both figures dependent on the partial oxygen pressure $p_{O2}$, and for simplicity a linear relationship has been assumed. The five straight lines in FIGS. 4 and 5 represent five different temperatures between 20 and 30 degrees Celsius. The detector signals decrease with increasing temperature. It is assumed that each detector supplies one measured signal. Due to the undefined temperature, these signals correspond to a region $\Delta 1$ or $\Delta 2$ on the $p_{O2}$ axes in FIGS. 4 and 5. When the smaller region, $\Delta 1$ in the present case, is included in the graph shown in FIG. 5, it is apparent that all temperatures are no longer admissible. In other words, the possible temperature range is diminished. As a result thereof, the $p_{O2}$ region is again reduced in accordance with FIG. 4 with the temperature being further restricted as in FIG. 5, and so on. The two parameters may thus be identified with sufficient precision by repeated application of these steps.

Selection of the analysis method explained in connection with FIG. 3 or the method explained in connection with FIGS. 4 and 5, will depend, among other things, on whether a sufficiently exact equation can be determined for specific parameters, particularly when there are more than two parameters, as well as on the extent of calculating outlay which can be permitted in order to still obtain the desired values within a few milliseconds.

If the oxygen absorption, the $CO_2$ concentration, the $CO_2$ production, the pressure, the gas flow rate, and the respirator quotients are also measured or identified in addition to the oxygen conctentration, a complete picture of the conditions present in the ventilation of a patient is obtained.

The method and apparatus disclosed herein may be advantageously used for undertaking other types of measurements. If, for example, the percentage of oxygen content is constant, such as is the case in the earth's atmosphere, the amount of oxygen coming into contact with the luminescent layer varies with the pressure. In addition to temperature, gas pressure can also be measured by the method disclosed herein, the apparatus making an excellent barometer. If a layer whose luminescent properties depend on humidity is selected, a fast and exact hygrometer results.

Good conditions can be created for all measurements by selecting the excitation wavelength, the filter characteristics, and the layer properties. For example, blood oxygen content can be rapidly identified by a small catheter with the use of water-insensitive layers. If integrated in a heart pacemaker electrode, a physiological control parameter can be measured.

The equation above is a semi-empirical formula based on the Sternvolmer equation.

$$s = i/(1 + k \cdot p)$$

where k is a constant and p is the partial pressure of the quencher. Even though it has proved to work well in one case, it might be necessary to use other equations when using other combinations of dyestuff/carrier materials.

The method and apparatus disclosed herein are not limited to the embodiments shown in the drawings and described in the text, but may be modified within broad limits by persons of ordinary skill. For example, luminescent layers may be utilized which are composed of a number of combinations of dyestuff/carrier material, each combination reacting to one or some of the characteristics of interest. The different combinations may be disposed separately within the luminescent layer. Excitation can be undertaken by a common light source, or by means of various different light sources.

We claim:

1. A method for rapidly measuring the magnitude of at least one characteristic of a sample medium in the presence of other characteristics in said sample medium comprising the steps of:
    bringing said sample medium once into contact with a luminescent layer having luminescent properties which vary over a wavelength spectrum as a function of said one characteristic and said other characteristics, said wavelength spectrum including a known wavelength region in which said one characteristic and said other characteristics differently influence the luminescent of light emitted by said luminescent layer;
    directing light of a defined wavelength and spectrum onto said luminescent layer thereby causing said luminescent layer to emit light over said wavelength spectrum;
    detecting the luminescent intensity of the emitted light from said luminescent layer in a plurality of different wavelength regions in said wavelength spectrum equal to the total number of said one and said other characteristics and including said known wavelength region and generating respective intensity signals for each of said different wavelength regions; and
    processing said intensity signals from each of said wavelength regions including identifying and measuring an intensity signal in said known wavelength region thereby to identify said one characteristic.

2. A method as claimed in claim 1 comprising the additional step of:
    maintaining constant the spectral distribution of said light directed onto said luminescent layer.

3. A method as claim in claim 1 comprising the additional step of:
    maintaining constant the intensity of said light directed onto said luminescent layer.

4. A method as claimed in claim 1 comprising the additional steps of:
    detecting the luminescent intensity of light from said luminescent layer in a selected wavelength region; and
    using the intensity of said light in said selected wavelength region as a reference signal for standardizing the luminescent intensities detected in the other wavelength regions.

5. A method as claimed in claim 1 comprising the additional step of:
    pulsing said light directed onto said luminescent layer.

6. A method as claimed in claim 1 for rapidly identifying two characteristics X1 and X2 from detector signals $S_i$, wherein i=1, 2, wherein the step of processing said detector signals is undertaken according to the formula $$S_i = \frac{i_i}{1 + k_i X_1} + b_i X_2 + a_i$$

wherein $i_i$ is the luminescent intensity in the wavelength region being detected at a defined value of $x_1$, $a_i$ is the background intensity, and $k_i$ and $b_i$ are approximation coefficients.

7. A method as claimed in claim 6 wherein the defined value of $X_1$ is $X_1 = 0$.

8. A method as claimed in claim 6 wherein $X_1$ is the partial oxygen pressure in said sample medium and wherein $X_2$ is the temperature of said sample medium.

9. A method as claimed in claim 1 comprising the additional steps of:
    alternatingly activating and deactivating a light source for directing said light on said luminescent layer; and
    alternatingly activating and deactivating a plurality of detectors for detecting said luminescent intensity synchronously with activating and deactivating said light source.

10. A method as claimed in claim 8 further defined by:
    simultaneously activating said light source and said detectors, and deactivating said detectors before deactivating said light source.

11. An apparatus for rapidly measuring the magnitude of at least one characteristic of a sample medium in the presence of other characteristics in said sample medium comprising:
    a luminescent layer having luminescent properties which vary over a wavelength spectrum as a function of said one characteristic and said other characteristics, said wavelength spectrum including a known wavelength region in which said one characteristic and said other characteristics differently influence the luminescent intensity of light emitted by said luminescent layer;
    means for bringing said sample medium once into contact with said luminescent layer;
    means for directing light of a defined wavelength and spectrum onto said luminescent layer thereby causing said luminescent layer to emit light over said wavelength spectrum;
    means for detecting the luminescent intensity of light from said luminescent layer in a plurality of different wavelength regions in said wavelength spectrum equal to the number of the total of said one characteristic and said other characteristics and including said known wavelength region and generating respective intensity signals for each of said different wavelength regions; and
    means for processing said intensity signals from said means for detecting for each of said wavelength regions for identifying and measuring an intensity signal in said known wavelength region, thereby to identify said one characteristic.

12. An apparatus as claimed in claim 11 wherein said means for directing light onto said luminescent layer is a plurality of light emitting diodes connected in series.

13. An apparatus as claimed in claim 11 wherein said means for directing light onto said luminescent layer is a plurality of light emitting diodes connected in parallel.

14. An apparatus as claimed in claim 11 wherein said means for directing light onto said luminescent layer includes a light source, and a means for pulsing said light source.

15. An apparatus as claimed in claim 14 wherein said means for directing light onto said luminescent layer further includes means for maintaining current supplied to said light source constant.

16. An apparatus as claimed in claim 15 further including means for varying the pulse duration of said light source.

17. An apparatus as claimed in claim 15 wherein said means for directing light onto said luminescent layer further includes means for varying the current supplied to said light source during the pulses on said light source.

18. An apparatus as claimed in claim 11 wherein said means for directing light includes a light source, and wherein said means for detecting the luminescent intensity of said light detects said intensity in two wavelength regions, further comprising:
means for forming a quotient of said intensities of said two wavelength regions and for controlling said light source in response thereto.

19. An apparatus as claimed in claim 11 wherein said means for directing light includes a light source and wherein said means for detecting includes a plurality of detectors corresponding to said plurality of different wavelength regions, and further comprising:
means for pulsing said light source; and
means for pulsing said detectors synchronously with the pulsing of said light source.

20. An apparatus as claimed in claim 19 wherein the beginning of each pulse for said light source and the beginning of each pulse for said detectors are synchronized, and wherein the pulse duration for said detectors is less than the pulse duration of said light source.

21. An apparatus as claimed in claim 20 further comprising:
means for generating a reference signal from said light source and for controlling the pulse duration of said detectors based on said reference signal.

22. An apparatus as claimed in claim 11 wherein said means for directing light onto said luminescent layer includes a light source and further comprising:
means for pulsing said light source;
means for monitoring a selected parameter of said light source during a pulse thereof; said diodes based on said monitored parameter.

23. An apparatus for rapidly measuring the magnitude of at least one characteristic of a sample medium in the presence of other characteristics in said sample medium comprising:
a luminescent layer having luminescent properties which vary over a wavelength spectrum as a function of said one characteristic and said other characteristics, said wavelength spectrum including a known wavelength region in which said one characteristic and said other characteristics differently influence the luminescent intensity of light emitted by said luminescent layer;
means for bringing said sample medium once into contact with said luminescent layer;
a plurality of diodes for directing light of a defined wavelength and spectrum onto said luminescent layer thereby causing said luminescent layer to emit light over said wavelength spectrum;
a plurality of filters having different bandpass regions, said plurality of filters being equal to the number of the total of said one characteristic and said other characteristics, and the bandpass region of one of said filters being selected in said known wavelength;
a plurality of detectors equal to the plurality of filters said filters respectively disposed between said sample and said detectors and said detector generating respective intensity signals for each of said different wavelength regions; and
means for processing the intensity signals from said plurality of detectors for identifying and measuring an intensity signal in said known wavelength region, thereby to identify said one characteristic.

24. An apparatus as claimed in claim 23 further comprising:
means for monitoring a selected operating parameter of said plurality of diodes and for controlling the operation said diodes based on said monitored parameter.

25. An apparatus as claimed in claim 24 wherein said monitored parameter of said diodes is the operating voltage of said diodes, and further comprising:
a current supply for said diodes;
a potentiometer for measuring said operating voltage of said diodes; and
a feedback loop for operating said current supply in response to said operating voltage.

26. An apparatus as claimed in claim 24 wherein said monitored parameter is the luminous intensity over the entire spectrum of said diodes, and further comprising:
means for detecting said luminous intensity over said entire spectrum of said diodes;
a current supply for operating said diodes; and
a feedback loop from said means for detecting said luminous intensity of said diodes to said current supply for controlling said current supply in response to said luminous intensity.

27. An apparatus as claimed in claim 24 wherein said monitored parameter of said diodes is the luminous intensity of said diodes in a selected wavelength region, and further comprising:
means for detecting the luminous intensity of said diodes in said selected wavelength region;
a current supply for operating said diodes; and
a feedback loop from said means for detecting said luminous intensity of said diodes at said selected wavelength region to said current supply for controlling operation of said current supply in response to said detected luminous intensity in said selected wavelength region.

28. An apparatus as claimed in claim 23 further comprising:
an additional filter disposed between said diodes and said luminescent layer.

29. An apparatus as claimed in claim 28 wherein said means for bringing said sample medium into contact with said luminescent layer is disposed for bringing said sample medium into contact with said luminescent layer between said luminescent layer and said additional filter.

30. An apparatus as claimed in claim 28 further comprising:
a light-tight housing enclosing said diodes, said filters, said additional filters, and said plurality of detectors.

* * * * *